(12) United States Patent
Gottlieb

(10) Patent No.: US 7,632,818 B2
(45) Date of Patent: Dec. 15, 2009

(54) METHOD FOR TREATING CONDITIONS ASSOCIATED WITH THE METABOLIC SYNDROME (SYNDROME X)

(76) Inventor: Marise S. Gottlieb, 215 Chestnut Hill Rd., Chestnut Hill, MA (US) 02467

( * ) Notice: Subject to any disclaimer, the term of this patent is extended or adjusted under 35 U.S.C. 154(b) by 307 days.

(21) Appl. No.: 10/804,954

(22) Filed: Mar. 19, 2004

(65) Prior Publication Data
US 2004/0186059 A1    Sep. 23, 2004

Related U.S. Application Data

(60) Provisional application No. 60/455,881, filed on Mar. 20, 2003.

(51) Int. Cl.
*A61K 38/00* (2006.01)
(52) U.S. Cl. .......................... 514/18; 514/19
(58) Field of Classification Search ................ None
See application file for complete search history.

(56) References Cited

U.S. PATENT DOCUMENTS

| | | | |
|---|---|---|---|
| 4,127,534 A | 11/1978 | Coy et al. | |
| 4,468,379 A | 8/1984 | Gottlieb | |
| 4,537,878 A | 8/1985 | Plotnikoff | |
| 4,616,079 A | 10/1986 | Gottlieb | |
| 4,699,898 A * | 10/1987 | Gottlieb | 424/278.1 |
| 4,710,380 A * | 12/1987 | Gottlieb | 424/278.1 |
| 4,778,750 A | 10/1988 | Gottlieb | |
| 4,874,608 A | 10/1989 | Gottlieb | |
| 5,000,936 A * | 3/1991 | Chibret | 424/43 |
| 5,013,546 A * | 5/1991 | Gottlieb et al. | 424/85.1 |
| 5,081,108 A | 1/1992 | Gottlieb | |
| 5,093,321 A | 3/1992 | Gottlieb | |
| 5,100,663 A * | 3/1992 | Gottlieb | 424/229.1 |
| 6,136,784 A * | 10/2000 | L'Italien et al. | 514/12 |

FOREIGN PATENT DOCUMENTS

EP    0 230 052 A2 * 12/1986

OTHER PUBLICATIONS

Persselin et al. Diagnosis of Rheumatoid Arthritis. Clin Orthop Relat Res. 1991. vol. 265, pp. 73-82.*
Harris et al. Prevalence of Diabetes, Impaired Fasting Glucose, and Impaired Glucose Tolerance in U.S. Adults. The Third National Health and Nutrition Examination Survey, 1988-1994. Diabetes Care, Apr. 1999. Vol. 21, No. 4, pp. 518-524.*
Fletcher et al. Plasma Fibrinogen and the Sedimentation Rate in Rheumatoid Arthritis and their response to the Administration of Cortison and Adrenocorticotropic hormone (ACTH). JCI. Jun. 1952. vol. 31, No. 6, pp. 561-571.*
Grundy et al. Definition of Metabolic Syndrome: Report of the National Heart, Lung, and Blood Institute / American Heart Association Conference on Scientific Issues Related to Definition. Circulation. 2004:vol. 109, pp. 433-438.*
Brennan et al. Role of pro-inflammatory cytokines in rheumatoid arthritis. Springer Semin Imuunopathol 1998 20: 133-147.*
Marise S. Gottlieb et al., "Diabetes Mellitus in Twins", DIABETES, vol. 17, No. 11, pp.693-704, Nov. 1968.
Ranjana Sinha et al., "Prevalence of Impaired Glucose Tolerance Among Children and Adolescents with Marked Obesity", The New England Journal of Medicine, vol. 346, No. 11, pp. 802-810, Mar. 14, 2002.
Gary L. Henriksen, "Serum Dioxin and Diabetes Mellitus in Veterans of Operation Ranch Hand", Epidemiology, vol. 8, No. 3, pp. 252-258, May 1997.
Jean-Charles Schwartz, "Biological Inactivation of Enkephalins and the role of Enkephalin-Dipeptidyl-Carboxypeptidase ("Enkephalinase") as Neuropeptidase", Enkephalin Metabolism, vol. 29, No. 17, pp. 1715- 1740, 1981.
Boulos Zacharie et al., "Thioamides: Synthesis Stability, and Immunological Activities of Thianalogues of Imreg. Preparation of New Thiacylating Agents Using Fluorobenzimidazolone Derivatives", J. Med. Chem. 42, pp. 2046-2052, 1999.
Holger Kayser et al.,"Stimulation of human peripheral blood lymphocytes by bioactive peptides derived from bovine milk proteins", FEBS Letters 383, pp. 18-20, 1996.
Paul M Ridker et al., "C-Reactive Protein, the Metabolic Syndrome, and Risk of Incident Cardiovascular Events 'An 8-Year Follow-Up of 14719 Initially Healthy American Women'", Circulation, 107, pp. 391-397, 2003.
Ripudaman S. Hundal et al., "Mechanism by which high-dose aspirin improves glucose metabolism in type 2 diabetes", The Journal of Clinical Investigation, vol. 109, No. 10, pp. 1321-1326, May 2002.
Manse S. Gottlieb et al., "Response to Treatment with the Leukocyte-derived Immunomodulator IMREG-1 in Immunocompromised Patients with AIDS-related Complex", Annals of Internal Medicine, 115, pp. 84-91, 1991.

* cited by examiner

*Primary Examiner*—Cecilia Tsang
*Assistant Examiner*—Marcela M Cordero Garcia
(74) *Attorney, Agent, or Firm*—Robert E. Bushnell, Esq.

(57) ABSTRACT

The present invention is directed to a method for treating individuals having inflammation or preventing inflammation in individuals at risk for inflammation, more specifically individuals with chronic inflammation as evidenced by elevated C-reactive protein, serum fibrinogen, elevated platelet count and platelet activity, elevated blood glucose, any component or combination of components of the metabolic syndrome by using the selected immunoregulators. The present invention also includes a method for preventing the development of inflammation in individuals at risk for inflammation by using the selected immunoregulators, and for deferring progression of the inflammatory state to the more specific outcomes of the Metabolic Syndrome including diabetes mellitus, coronary heart disease, and cancer.

13 Claims, No Drawings

METHOD FOR TREATING CONDITIONS ASSOCIATED WITH THE METABOLIC SYNDROME (SYNDROME X)

CLAIM OF PRIORITY

This application makes reference to, incorporates the same herein, and claims all benefits accruing under 35 U.S.C. §119 and §120 from a provisional application for Treatment of Type II Diabetes and Other Conditions Associated with the Metabolic Syndrome (Syndrome X), a Disease of the Innate Immune System, with a Unique Immunomodulator earlier filed in the U.S. Patent & Trademark Office on 20 Mar. 2003 and there duly assigned Ser. No. 60/455,881.

BACKGROUND OF THE INVENTION

1. Field of the Invention

The present invention relates to a method for treating individuals having inflammation or preventing inflammation in individuals at risk for inflammation, more specifically individuals with chronic inflammation as evidenced by elevated acute phase reactants including C-reactive protein and serum fibrinogen, elevated platelet count or platelet activity, elevated blood glucose, or any component or combination of components of the metabolic syndrome, from progressing to the natural outcome of the syndrome, such outcome being diabetes mellitus, coronary artery disease, and related complications of diabetes mellitus 2. Description of the Related Art The distribution of fat characteristic of the Metabolic Syndrome (Syndrome X) (a precursor to a form of Type II Diabetes) resembles the lipodystrophy seen in longer term HIV Disease survivors, and which is also associated with insulin resistance. There is currently a debate as to whether the cause of lipodystrophy and abnormal glucose tolerance in HIV survivors is due to treatment with protease inhibitors, or to long-term survival with HIV infection. There is clearly continual antigenic stimulation in this situation. Chronic antigenic stimulation results in inflammation which, in turn, can result in abnormal immune function, cardiovascular disease, and other sequelae.

Earlier studies had described that Type II diabetes had a very strong familial (dominant) inheritance pattern (GOTTLIEB AND ROOT, *DIABETES* 17:693-704, 1968). Current Type II diabetes, associated with the Metabolic Syndrome, has not been reported to have such a familial association (SINHA, ET AL., *N. ENGL. J. MED*. 346:802-810, 2002).

Studies have shown an increase in coronary heart disease mortality in association with air pollution and increased diabetes mellitus in association with release of dioxins (for example, HENRIKSEN, G L, EPIDEMIOLOGY 8:252-8(1097)). C-Reactive Protein levels have been elevated in these studies. (Elevated C-Reactive Protein is a marker for an inflammatory response.) The frequency of obesity has been increasing markedly in all populations.

Therefore, chronic antigenic stimulation, whether by infection or environmental pollutants can overwhelm the innate immune system's ability to control (remove) these substances leading to uncontrolled inflammation, failure of insulin to affect liver and muscle enzymes to control blood glucose, leading to impaired glucose tolerance, hyperinsulinemia, insulin resistance, dyslipidemia, elevated triglycerides, and i.e. the Metabolic Syndrome.

This invention concerns the relationship between cell-mediated immunity and pathological conditions associated with cell-mediated immune dysfunction. Such conditions include HIV Disease and other chronic infectious diseases caused by particular pathogenic organisms, including HIV, gingivitis, candida sp., those caused by chronic inflammation resulting from exposure to environmental toxins and particulates, and those resulting from other stressors such as trauma and aging. The invention also concerns other conditions in which there is dysfunctional immunity resulting in metabolic and inflammatory conditions.

A typical manifestation of cell-mediated immunity is the delayed type hypersensitivity ("DH") skin reaction. A DH skin reaction is observed when an appropriate antigen is injected intradermally. Within 24 to 48 hours, local inflammation (erythema) and a swelling and thickening (induration) are observed in a sensitive individual. The degree of sensitivity may be measured by the size and severity of the reaction. The DH reaction also presents characteristic histological findings—specifically, perivascular infiltration of leukocytes in the inflamed area. The cells seen at the site of a DH reaction are derived from the peripheral blood leukocyte population.

The mechanisms of cell-mediated immunity are as yet incompletely understood. It is known that the cells which mediate the response are capable of responding in a variety of ways to a challenge from an antigen. These responses include: proliferation of cells bearing specific sensitivity to a given antigen; the induction and multiplication of cells mediating a variety of immune functions, including antibody production; and reactions against foreign cells, tumors, and other foreign substances.

The present invention relates to the use of (1) endogenous regulators of the immune system, which are isolated from dialyzed extracts of leukocytes, and synthetic similar products; and (2) compositions containing the immunoregulators. These immunoregulators, whether produced endogenously by the human individual or provided exogenously as a therapeutic agent, profoundly affect the quality and quantity of cell-mediated immunity responses; and are useful in the treatment of clinical conditions characterized by inadequate or inappropriate reaction to antigens including, but not limited to HIV Disease, rheumatoid arthritis, sarcoidosis, and malignancy.

Earlier A. Arthur Gottlieb Patents: In A. Arthur Gottlieb U.S. Pat. No. 4,468,379, it was disclosed that endogenous materials exist that amplify the speed and magnitude of the cell-mediated immune system response. These amplifier materials are distinguished from so-called transfer factors in that amplifiers do not transfer to a subject an immune response to a mitogen or antigen to which the subject has not previously been exposed and is not concurrently exposed, while transfer factors are said to do so. Moreover, amplifiers nonspecifically increase cell-mediated immune system responses to mitogens and antigens to which the subject has previously been or concurrently is exposed, while transfer factors are specific to particular antigens.

The material designed "amplifier 1" in the '379 patent is now known by the inventor to be a mixture of various things. They include what is referred to subsequently in the present patent application as YG-material and what is referred to subsequently in the present patent application as YGG-material. It was suggested in A. Arthur Gottlieb U.S. Pat. No. 4,616,079 that amplifiers appear to act on T-helper cells (T4 cells) in a way that causes them to produce chemical mediators (lymphokines) whose effect is to increase the speed and/or magnitude of cell-mediated immune system response to antigens and other means of activating a cell-mediated immune system response. (The term "recall antigen," as used hereinafter, refers to an antigen to which a subject has previously been exposed.) Indicia of this response include DH reaction to recall antigens, production of IL-2 and gamma interferon, and potentiation of cytotoxic cells.

It is known that various diseases and pathological conditions, such as HIV Disease (also referred to as Acquired Immune Deficiency Syndrome (AIDS) and AIDS-Related Complex (ARC)), as well as other infectious agents, chemotherapy, radiation, aging, other forms of physiologic and psychological stress, and environmental exposures depress the immune system response. As a result, there is increased susceptibility to opportunistic infections, malignancies, and other pathological conditions that a normal immune system would have confronted. Frequently (and for some conditions, invariably), the result is death. Administration of immunoregulators (referred to as "amplifiers" in other A. Arthur Gottlieb patents, including U.S. Pat. No. 5,100,663) provides a means of improving cell-mediated immune system responsiveness, where the cell-mediated immune system remains sufficiently intact for it to respond to such challenge.

Earlier A. Arthur Gottlieb patents describe means of extracting amplifier materials from human leukocyte dialysates by reverse-phase HPLC processes. A. Arthur Gottlieb U.S. Pat. No. 4,699,898, as well as in other related patent applications of the inventor, including U.S. Pat. No. 5,100,663, the inventor disclosed his discovery of peptide products containing Tyr-Gly (YG) and Tyr-Gly-Gly (YGG) amino acid residue sequences, that are immunologically active components in the partially purified dialysate fractions previously described in earlier A. Arthur Gottlieb patents, such as A. Arthur Gottlieb U.S. Pat. No. 4,616,079.

Earlier A. Arthur Gottlieb patents did not teach that the YG and YGG peptides had any effect on the consequences of chronic antigenic stimulation, including inflammation, inflammatory disease, metabolic alterations, or on regulation of indicators of such consequences including elevated C-Reactive Protein, fibrinogen, sialic acid, or blood glucose.

The earlier A. Arthur Gottlieb patents may also be consulted for other general background information on immunoregulators (the same as what are called immunoamplifiers, amplifiers, or immunomodulators in those patents) and their use.

Coy: Coy U.S. Pat. No. 4,127,534 describes tripeptides of the form Tyr-X-Gly, where X is a D-amino acid. Coy asserts that these products have analgesic and related utility, as indicated by rat tail flick or other tests; accordingly, they may be used as substitutes for such medications as aspirin and sedatives. Coy claims pharmaceutical compositions that contain a "therapeutically effective amount" of Tyr-X-Gly, including Tyr-D-Ala-Gly. Coy asserts in the body of his specification that a therapeutically effective amount of the product for purposes of the disclosed utility is from 0.001 mg per kg of bodyweight to 100 mg per kg of bodyweight, administrated daily. (Extrapolated to an 80 kg person, this amounts to a daily dose of approximately 0.1 mg to 10 g; 0.1 mg is equivalent to approximately 300 nanomoles, and 10 g is equivalent to approximately 0.03 moles.) It should be noted that the relevant language of Coy's specification is in the present tense, indicating use of prophetic examples. (No therapeutic examples are provided in the specification, and no statements about utility or dosage are made in the past tense.)

Coy does not assert any immunological use of the products. Coy does not describe any of the D-amino acid group as a means of preventing cleavage of the Tyr-Gly bond by endogenous enzymes. Coy does not describe any utility for doses of less than the aforesaid minimum daily amounts (0.001 mg/kg, 0.1 mg, and 300 nM).

Plotnikoff: Plotnikoff U.S. Pat. No. 4,537,878 discloses and claims the use of endogenous endorphins and enkephalins to stimulate the immune system. The dosage amounts actually used in vivo (Plotnikoff's Examples VIII to XI) were from 1 microgram (µg) per kg to 50 µg/kg, single i.v. dose. Elsewhere, however, Plotnikoff refers to a therapeutic dose of from 1 µg/kg to 30 mg/kg, and to a preferable dosage rate of from 0.01 fg/kg to 250 µg/kg. No explanation is given for the inconsistencies, and no data in the specification indicates a reason why these latter dosage rates were mentioned or claimed. (They do not appear in examples or similar data.)

The molecular species whose use Plotnikoff discloses are the endogenous enkephalin pentapeptides, and longer endorphin polypeptide extensions thereof (extended from the C-terminal end). Plotnikoff does not disclose use of any non-endogenous peptides, nor anything concerning use of dipeptides, tripeptides, or tetrapeptides. Plotnikoff does not indicate that Tyr-Gly or Tyr-Gly-Gly have any immunological or other utility. Plotnikoff does not show that any products, other than enkephalin, have utility in treating AIDS or ARC.

Schwartz: Schwartz et al., Biological inactivation of enkephalins and the role of enkephalin-dipeptidyl-carboxypeptides ("enkephalinase") as neuropeptidase, ENKEPHALIN METABOLISM 29:1715 (1981), extensively reviews work that has been done in the field of enzymatic breakdown of enkephalins. Schwartz summarizes the paper as follows:

In this review it will be shown that enkephalins are rapidly hydrolyzed in vivo and that several peptidase activities have been identified which are able to cleave these molecules to give various biologically-inactive fragments. (Emphasis added.)

Schwartz et al. and the work summarized in the review teach that various endogenous enzymes cleave (hydrolyze) the Gly-Phe, Gly-Gly, and Tyr-Gly bonds of endogenous mammalian polypeptides, such as Leu-enkephalin and Met-enkephalin into what Schwartz alleges are "biologically inactive fragments." Such fragments include what Schwartz refers to as Tyr-Gly, which in context apparently means a dipeptide containing Tyr and Gly amino acid residues, in that order. But Schwartz does not indicate what side chains or other groups, if any, are attached to the amino acid residues or what specific molecular structure is present in the Tyr-Gly product.

Schwartz and the work summarized in the review also disclose various means of inhibiting such enzymatic cleavage, including N-methylation of the Tyr residue; esterification, amidification, and alcoholation of the C-terminal carboxyl; insertion of a D-amino acid residue (such as D-Ala) into the chain near the C-terminal end; and mixture with bacitracin, puromycin, bestatin, amastatin, or thiorphan. (It is also known in pharmaceutical art, although not discussed in Schwartz, to bind or complex an enzyme-inhibiting agent to a therapeutically active molecule, so that the agent will preferentially bind to the active site on the enzyme that is to be inhibited, thereby preempting that site and thus keeping the enzyme from hydrolyzing the molecule to be protected. This is exemplified by the use of the product sulbactam, a beta-lactamase inhibitor used to protect ampicillin from beta-lactamase; thus, UNA-SYN.™. (Pfizer) is a mixture of sulbactam and ampicillin, while sultamicillin is ampicillin complexed or otherwise linked with sulbactam via an ester. It is also known, for example in the case of the synthetic penicillins, to introduce a large group (such as methyl) at a location on a therapeutically active molecule where there would otherwise be a space providing a site for enzyme attachment, which results in hydrolysis. The result of occupying such a space is to inhibit enzymatic degradation of the molecule thus protected.)

The Schwartz paper does not mention any immunological activity or other utility of the allegedly useless and biologically inactive fragments resulting from enzymatic action on enkephalins.

Delivery of drug via hydrolysis: It is known that a therapeutically active molecule may be delivered by administering to a patient a different molecule that hydrolyzes, as a result of the action of endogenous enzymes, to fractions that include the desired therapeutically active molecule. Perhaps hetacillin is the best known example. Hetacillin breaks down in the human body to ampicillin. A legal controversy ensued internationally, following the introduction of hetacillin, over whether the manufacture, use, and sale of hetacillin infringed patents on ampicillin.

Zacharie: Zacharie, et al. (J. MED. CHEM. 42:2046 (1999).) have confirmed the work of A. Arthur Gottlieb, as previously described, by testing Tyr-Gly and Tyr-Gly-Gly peptides for biologic activity in vitro. Additionally, Zacharie, et al. made covalent modifications to these molecules, as taught by A. Arthur Gottlieb, by thioacylating the molecules, thereby increasing biologic activity.

Kayser and Meisel: A. Arthur Gottlieb's teachings concerning the biologic activity of Tyr-Gly and Tyr-Gly-Gly have also been confirmed by Kayser and Meisel (FEBS LET. 383: 18 (1996)) who show, by in vitro testing, that these peptides which can also be derived from the breakdown of certain milk proteins are immunologically active molecules.

Commercial Tyr-Gly: Tyr-Gly is sold as a chemical reagent (L-tyrosylglycine) by Sigma Chemical Co., St. Louis, Mo., among others. Tyr-Gly is not sold in U.S.P. grade, and it is illegal under applicable laws to sell Tyr-Gly for use as a pharmaceutical. Commercial grade Tyr-Gly is not considered free of pyrogens, endotoxin, and other pharmaceutically unacceptable constituents. The presence of such pyrogens, endotoxin, and other pharmaceutically unacceptable constituents makes a product unacceptable for use as a drug, as that term is defined by federal statute, both under generally recognized medical principles and under FDA regulations. To the extent of the inventor's knowledge, no pharmaceutical preparations of this product are or have been available.

Commercial Tyr-Gly-Gly: Tyr-Gly-Gly is sold as a chemical reagent (L-tyrosylglycylglycine) by Sigma Chemical Co., St. Louis, Mo., among others. Tyr-Gly-Gly is not sold in U.S.P. grade, and it is illegal under applicable laws to sell Tyr-Gly-Gly for use as a pharmaceutical. Commercial grade Tyr-Gly-Gly is not considered free of pyrogens, endotoxin, and other pharmaceutically unacceptable constituents. The presence of such pyrogens, endotoxin, and other pharmaceutically unacceptable constituents makes a product unacceptable for use as a drug, as that term is defined by federal statute, both under generally recognized medical principles and under FDA regulations. To the extent of the inventor's knowledge, no pharmaceutical preparations of this product are or have been available.

SUMMARY OF THE INVENTION

It is an object of the present invention is to provide a method for treating individuals with chronic inflammation as evidenced by elevated C-Reactive Protein, serum fibrinogen, and/or blood glucose level.

It is another object of the present invention to provide a method for preventing chronic inflammation.

It is also an object of the present invention to provide a method for treating or mitigating a symptom in a patient with a symptom of chronic inflammation or an inflammation-related metabolic disturbance.

It is also an object of the present invention to provide a method to interfere with and/or control the progression of a patient from the Metabolic Syndrome, including Hypertension, to consequences of the Metabolic Syndrome, including but not limited to Diabetes Mellitus, Coronary Heart Disease, or Cancer. The Metabolic Syndrome has six major components, including elevated blood pressure, atherogenic dyslipidemia, abdominal obesity, insulin resistance with or without glucose intoloerance, a proinflammatory state, and a prothrombotic state (NATIONAL HEART BLOOD AND LUNG INSTITUTE).

It is further an object of the present invention is to provide a method of controlling blood glucose level, which is an indicator of insulin resistance in the diabetes mellitus characteristic of lipodystrophy associated with long term HIV Disease (or the Metabolic Syndrome ("Syndrome X")).

The present invention concerns the relationship between cell-mediated immunity and pathological conditions associated with cell-mediated immune dysfunction. Such conditions include HIV Disease and other chronic infectious diseases caused by particular pathogenic organisms, including HIV, tuberculosis, gingivitis, candidiasis, those caused by chronic inflammation resulting from exposure to environmental toxins and particulates, and those resulting from other stressors such as trauma and aging. The invention also concerns other conditions in which there is dysfunctional immunity resulting in metabolic and inflammatory conditions.

The present inventor has discovered that the selected immunoregulators may be used to control aspects of disease which heretofore have been attributed to a metabolic origin and thought to be controlled by treating the metabolic abnormality. This discovery represents the first indication that regulation of immunologic activity can control aspects of metabolism, in particular those which are affected by infectious, environmental and other exposures as well as psychological and other physiological stress.

DETAILED DESCRIPTION OF THE PREFERRED EMBODIMENTS

Definition

The "selected immunoregulators" ("selected immunormodulators" "selected immunoamplifiers") include the purified Leukocyte Dialysate Subfraction (LDS) described by Dr.

A. Arthur Gottlieb Patents (U.S. Pat. Nos. 5,100,663, 4,616,079, 4,699,898, 4,710,380, 4,778,750, 4,874,608, 5,013,546, 5,081,108, 5,093,321 which are incorporated herein by references) which is naturally derived from healthy human leukocytes, as well as purified immunologically active components of the naturally derived immunoregulators including the dipeptide tyrosylglycine (YG) and the tripeptide tyrosylglycylglycine (YGG), as well as synthetically produced YG and YGG. These regulators also include covalently modified YG and YGG, such modifications designed to stabilize or to enhance the biological activity of said regulators, as well as pharmaceutically acceptable salts, suitable for human use, of YG, YGG, and related molecules including covalently modified YG, and covalently modified YGG.

YG means Tyr-Gly (also known as L-tyrosylglycine). YGG means Tyr-Gly-Gly (also known as L-tyrosylglycylglycine).

YG-material (or YG-product) means a member of a group consisting of a set of molecular species wherein each molecule contains a Tyr-Gly amino acid residue sequence, and no other amino acid residues. The molecule may be in the form of a simple Tyr-Gly sequence, or the molecule may be methylated, amidified, esterified, acetylated, etc. YG-material does not include tripeptides or higher polypeptides. However, two YG-materials (e.g., two molecules of Tyr-Gly) may be complexed together in the form: (Tyr-Gly)Zn++(Tyr-Gly), or they may be dimerized as described in A. Arthur Gottlieb U.S. Pat. No. 5,100,663. Such a complex or dimer is not considered a tetrapeptide, but merely two dipeptides complexed together or dimerized.

YGG-material means a member of a group consisting of a set of molecular species wherein each molecule contains a Tyr-Gly-Gly amino acid residue sequence, and no other amino acid residues. The molecule may be in the form of a simple Tyr-Gly-Gly sequence, or the molecule may be methylated, amidified, esterified, acetylated, etc. YGG-material does not include dipeptides, tetrapeptides, or higher polypeptides. However, two YGG-materials (e.g., two molecules of Tyr-Gly-Gly), or YG-material and YGG-material, may be complexed together or dimerized. Such a complex or dimer is not considered a pentapeptide or hexapeptide.

Inhibited YG-material means YG-material that has been mixed, complexed, bound, linked, or otherwise combined with a means for inhibiting cleavage of the Tyr-Gly bond of the molecule by endogenous enzymes; however, the material must still contain a Tyr-Gly amino acid residue sequence and no other amino acid residue sequence. Puromycin and bacitracin are examples of inhibitors that may be mixed with YG-material. It is also known to N-methylate the Tyr residue to inhibit enzymatic action. It is also known to esterify or amidify the C-terminal carboxyl group to inhibit enzymatic cleavage. The products of such expedients are hereinafter termed inhibited YG-material. Inhibited YG-material does not include expanded YG-material, as defined below; the two terms are mutually exclusive. Also, the term "inhibited YG-material" falls within the scope of the term "YG-material."

Expanded YG-material means a molecule of the form Tyr-X-Gly, where X is a D-amino acid, such as D-Ala. The term includes amides, esters, salts, etc., as in the case of YG-material. It is known that the insertion of a D-amino acid into Tyr-Gly tends to inhibit cleavage of the Tyr-Gly bond by endogenous enzymes. The terms YG-material and expanded YG-material are mutually exclusive, since the former is a dipeptide and the latter is a tripeptide; also the former has a Tyr-Gly bond and the latter does not.

Endogenous YG-material means YG-material produced within the body. Endogenous YGG-material means YGG-material produced within the body.

YG Product includes YG, YG Material, Inhibited YG Material, Expanded YG Material, and endogenous YG Material. YGG Product includes YGG Material, Endogenous YGG Material, and any covalent or other modification to said YGG, and any salt of any of these.

Extraneous-peptide amino acid residue sequences means any and all amino acid residue sequences except Tyr-Gly and Tyr-Gly-Gly. As used herein, "sequence" refers to a plurality of residues, and the terms excludes a molecule with only a single amino acid residue, such as glycine.

The Metabolic Syndrome is a constellation of characteristics which may include obesity, hypertension, insulin resistance, hyperinsulinemia, impaired glucose tolerance, atherogenic dyslipidemia, including elevated serum triglycerides and low serum HDL cholesterol levels, and elevated Fibrinogen and C-Reactive Protein, coagulation disorders, acanthosis nigricans and polycystic ovary syndrome. The most prevalent current hypothesis regarding causation is that the metabolic syndrome, which is present in 25% of the population is secondary to overeating and lack of physical exercise, characteristic of the modern lifestyle. It is possible that the metabolic syndrome is initiated by chronic antigenic stimulation and then the adipose tissue becomes a depot for further antigenic substance accumulation such as occurs with exposure to fine particle air pollution, dioxin from burning of plastics, or from tobacco smoke and the cycle reinforces itself since adipose tissue secretes increased levels of cytokines, causing dyslipidemia and other effects associated with the Metabolic Syndrome. The process then becomes self-perpetuating with obesity leading to insulin resistance, elevated triglycerides, impaired glucose tolerance, etc.

The presence of the acute phase reactants fibrinogen and C-Reactive Protein, markers for that inflammation, draws one's attention to look for the cause of the inflammation, and to postulate that the underlying pathology may be caused by a chronic inflammatory state, whether it is induced by antigens associated with environmental factors or by chronic infection which overwhelms the ability of the innate immune system to remove them. Moreover, the association of coronary heart disease with elevated cholesterol levels, as causative, is now brought into question, given the observation that elevated C-Reactive Protein is a better predictor of coronary heart disease than elevated cholesterol (RIDKER, P M, ET AL. *CIRCULATION* 107:391-7 (2003). Cholesterol is a necessary component of intact cell membranes. Therefore, elevated serum cholesterol levels may be markers of cellular membrane disruption secondary to inflammation from either infectious or non-infectious antigenic stimulation, which then secondarily contribute to endothelial plaque and thrombus formation. It has been recognized that the HMG-CoA reductase inhibitors ("statin" drugs) lower cholesterol levels and decrease coronary heart disease mortality. These drugs are also anti-inflammatory. Regular use of aspirin has been reported to decrease coronary heart disease mortality. This reduction has been attributed to the anticoagulant effect of aspirin. However, aspirin is an anti-inflammatory agent, as well, and has been recently been desribed as facilitating blood glucose control in diabetes mellitus (for example, Hundal, RS, et al. Journal of Clinical Investigation. 109:1321-6 (2002).

"Stress," (either physiological or psychological, i.e., Type "A" personality) which decreases immune function may also contribute to coronary heart disease by enabling antigenic stimulation to proceed due to reduced ability to clear the "foreign" agent. Stress is known to increase production of corticosteroids, which, in turn, reduce functional immunity.

If chronic antigenic stimulation resulting from immune dysfunction is causal of the metabolic syndrome, then correction of immune dysfunction could reduce the symptoms and characteristics of the metabolic syndrome, and thus the factors leading to diabetes mellitus and coronary heart disease.

The instant application describes the use of the Selected Immunoregulators to affect metabolic aspects of certain disease conditions, including the "Type 2 Diabetes Mellitus" and other conditions found in association with or as a result of the Metabolic Syndrome, also known as Syndrome X, or caused by the same physiological basis as the Metabolic Syndrome (for example, HIV Lipodystrophy). The instant application will further describe the control of inflammatory effects of chronic antigenic stimulation. Such stimulation and inflammation may be caused by factors including but not limited to infectious pathogens and environmental pollutants such as particulates, organic materials, and cigarette smoke.

The effects of the immunomodulators have been demonstrated in both clinical and laboratory studies and include, but are not limited to the findings described below:

EXAMPLE 1

Improvement of Metabolic Syndrome and Consequences of Chronic Antigenic Stimulation The Metabolic Syndrome, or Syndrome "X", is a recently described illness which is characterized by obesity, insulin resistance, hypertension, dyslipidemia, decreased serum HDL-L, elevated serum triglycerides, impaired glucose tolerance, polycystic ovary syndrome, increased acute phase proteins, including C-Reactive Protein and fibrinogen, and leads to diabetes mellitus, coronary artery disease, and cancer. Coronary Heart Disease and Diabetes Mellitus have been reported to be increased in populations chronically exposed to air pollution and to dioxins. People who are long-term survivors with AIDS develop a lipodystrophy with features very similar to the Metabolic Syndrome. Both of these populations are subject to chronic antigenic stimulation.

There are data from a clinical trial in patients with HIV Disease, using the leukocyte-derived immunoregulator which has YG and YGG as the active components (GOTTLIEB, M S. ANNALS OF INTERNAL MEDICINE. 115:84 (1991)), which were not examined with regard to evaluation of the immunoregulator, that are useful with regard to the current thinking concerning the Metabolic Syndrome. Re-examination of some of the toxicity evaluation data collected during the clinical trial showed that during the course of the trial, mean serum glucose increased in those who received placebo (p<0.015) and became significantly higher than in those treated with the immunoregulator (p<0.043), which either declined if all subjects were included or rose slightly if only those subjects with normal values at baseline were included (Table 1).

Similarly, blood platelets which contribute to the coagulopathy associated with the Metabolic Syndrome, were "reduced" in treated patients and significantly increased in those receiving placebo (p=0.038). The between group difference was significant (p=0.032) (Table 1).

TABLE 1a

All Patients

| Serum Component | Treated | | | | Placebo | | | | Between Group |
|---|---|---|---|---|---|---|---|---|---|
| | N | Baseline[a] | Δ[b] | ±s.d | P-Value[c] | N | Baseline[a] | Δ[b] | ±s.d | P-Value[c] | P-Value[d] |
| Glucose | 94 | 84.89 | −5.67 | ±32.28 | 0.066 | 50 | 81.95 | +7.99 | ±33.25 | 0.186 | 0.043 |
| Platelets × (10³) | 97 | 204.81 | −1.81 | ±46.17 | 0.381 | 50 | 208.16 | +8.76 | ±39.54 | 0.038 | 0.032 |

TABLE 1b

Patients with Normal Baseline Values

| Serum Component | Treated | | | | Placebo | | | | Between Group |
|---|---|---|---|---|---|---|---|---|---|
| | N[e] | Baseline[a] | Δ[b] | ±s.d | P-Value[c] | N | Baseline[a] | Δ[b] | ±s.d | P-Value[c] | P-Value[d] |
| Glucose | 54 | 73.42 | +2.77 | ±15.73 | 0.556 | 31 | 72.07 | +8.61 | ±18.86 | 0.015 | 0.059 |
| Platelets × (10³) | 94 | 208.36 | −2.58 | ±46.24 | 0.304 | 49 | 210.56 | +7.78 | ±39.33 | 0.054 | 0.036 |

[a]The value at baseline is that at the start of treatment.
[b]Mean change from baseline at end of therapy.
[c]P-values correspond to the Wilcoxon Signed Rank Test Statistic.
[d]P-values correspond to the Mann-Whitney (Stratified Wilcoxon Rank Sum) Test Statistic.
[e]These patients had normal levels of component at baseline.

These findings support an hypothesis that uncontrolled and chronic antigenic stimulation due to infection (HIV is present in many tissues and cells once infection has occurred) or environmental pollutants, and the relative immunologic deficiency and failure to effectively remove such foreign material due to an overwhelming antigen and/or reduced immune function load may be contribute to the metabolic syndrome and insulin resistance which is a result of interference with insulin activity and the activity of enzymes related to glucose metabolism. Correction of such immune deficiency or dysregulation with the unique immunoregulators described herein appears to correct key components of the metabolic syndrome and lipoatrophic diabetes mellitus associated with HIV Disease. Based on these findings, it is possible, then to treat patients who have or who are at risk for the Metabolic Syndrome with one or more of the immunoregulators described herein, and thus to prevent the Diabetes Mellitus, Coronary Heart Disease, Cancer, and other outcomes associated with the Metabolic Syndrome which is seen in increasing frequency worldwide, and more so in areas of increased pollution, and in populations with high prevalence of and at high risk for chronic infections, e.g. tuberculosis and malaria, by improving the individual's immune function.

The further application of the instant invention is illustrated by the following forward looking examples.

EXAMPLE 2

Industrial Exposure

A group of employees in an industrial plant are repeatedly exposed to organic solvents and other reagents. The company physician realizes that prolonged exposure, even at low levels, may diminish immune function. The physician tests a number of employees and finds reduced DH responsiveness and increased C-Reactive Protein. He prescribes doses of an effective dose of YG Product (for example, 10 μg of YG to be taken at periodic intervals as determined by the physician, depending upon the patient's condition). The physician follows the employees' DH responsiveness and notes improvement. The physician also follows the employees' immune function using standard laboratory proliferative assays, testing the ability of Peripheral Blood Mononuclear Cells to respond to stimulation with certain antigens or mitogens. He also notes a decline in employee illness-related absence, elevated blood pressure and dyslipidemia.

EXAMPLE 3

Exposure to Jet Fuel

A military air wing is preparing for deployment to a combat zone. It is known that exposure to jet fuel suppresses immune function. The wing physician, knowing that the psychological stress of deployment also reduces immune function orders an effective dosage of YGG material to be taken periodically by each member of the group. He reasons that maintaining normal immune balance will avoid illnesses and infections commonly seen in military personnel under these conditions, thereby maintaining a higher level of troop readiness. He also knows that the immunosuppressive effects of exposure to jet fuel linger well beyond the initial period of exposure. He therefore orders continuation of YGG material upon return to the home base until he confirms the return of normal immune function. By doing so, he prevents sequelae of chronic inflammation such as the Metabolic Syndrome.

EXAMPLE 3

Control of Sequelae of Chronic Antigenic Stimulation by a Pathogen

A patient is treated for HIV Disease. His viral load decreases, however he begins to show signs of lipodystrophy and other indications of the Metabolic Syndrome. His physician is particularly concerned that the patient's glucose tolerance is abnormal, indicating possible onset of the "Type 2" Diabetes Mellitus and the other abnormalities associated with the Metabolic Syndrome, which lead to Coronary Heart Disease.

Also, recognizing that the patient's immune function is compromised and that chronic antigenic stimulation, and the resulting Metabolic Syndrome which could lead to insulin resistance, the physician prescribes 10 μg of YG product to be taken at periodic intervals, depending upon the patient's status, for the remainder of the patient's life, as HIV is known to incorporate itself into many different cells and tissues such that it cannot be totally eliminated. HIV Disease remains under control and the patient's glucose tolerance returns to normal.

EXAMPLE 4

Chronic Environmental Antigen Stimulation

A young woman presents to her physician, on annual physical examination, with a weight gain of 50 pounds, is found to have high blood pressure, and reports vaginal pruritis. Over the past few years, she has lived in an area of major traffic congestion (near an oil refinery). The physician does a physical examination and discovers unusual black pigmented areas in her neck creases (acanthosis nigricans) and orders laboratory tests, including fasting and 2-hour blood glucose, serum triglycerides, serum insulin, a cholesterol profile, C-Reactive Protein, serum fibrinogen, and a vaginal smear for candidiasis.

She is found to have impaired glucose tolerance, elevated serum triglycerides, low HDL and high LDL receptors and high C-Reactive Protein and fibrinogen levels. Her vaginal smear is positive for *candida albicans.*

The physician knows that he is seeing a case of the Metabolic Syndrome which progresses to Diabetes Mellitus and Coronary Heart Disease. He prescribes a weight reduction diabetic diet, physical exercise, an ACE Inhibitor, and Fluconazole. The patient reports losing weight and gaining it back.

Since the physician knows of the patient's prolonged and constant exposure to environmental antigens, and since refractory infection with candida albicans is a hallmark of immune dysfunction, he prescribes YG (sublingual) to be taken once every two weeks, in addition to continuation of the other recommendations.

The physician monitors her blood glucose, C-Reactive Protein, serum triglycerides, serum cholesterol, and weight, periodically.

Over the course of a year, her blood glucose changes toward normal, her C-Reactive Protein is reduced (indicating reduced inflammatory processes) and her cholesterol level is reduced. She continues her diet and physical exercise and loses weight. She requires less high blood pressure medication. The physician continues to monitor her cell-mediated immune function, blood glucose levels, lipid profile, and measures of inflammation, and adjusts her medications appropriately.

The patient continues to lose weight to reach her target weight, blood pressure is controlled, blood glucose is normalized, and her risk of diabetes mellitus and coronary heart disease is reduced.

As the preceding examples and discussion show, the invention can be practiced with a genus of products characterized by the presence of Tyr (Y) and Gly (G) amino acid residues, specifically di- and tripeptides containing Y and G amino acid residues, with optional admixture with other products and with optional modification of certain parts of the structure.

While the invention has been described in connection with specific and preferred embodiments thereof, it is capable of further modifications without departing from the spirit and scope of the invention. This application is intended to cover all variations, uses, or adaptations of the invention, following, in general, the principles of the invention and including such departures from the present disclosure as come within known or customary practice within the art to which the invention pertains, or as are obvious to persons skilled in the art, at the time the departure is made. It should be appreciated that the scope of this invention is not limited to the detailed description of the invention hereinabove, which is intended merely to be illustrative, but rather comprehends the subject matter defined by the following claims.

What is claimed is:

1. A method for controlling chronic inflammation associated with Metabolic Syndrome in an individual having the Metabolic Syndrome, comprising:
    administering to said individual an effective dosage of a pharmaceutical composition selected from the group consisting of YG-Product, YGG-Product, and a combination thereof.

2. The method of claim 1, wherein the chronic inflammation is evidenced by at least one of elevated C-Reactive Protein and elevated serum fibrinogen.

3. The method of claim 1, wherein the chronic inflammation is evidenced by at least one of elevated platelet count and elevated platelet activity.

4. The method of claim 1, wherein the individual has at least one condition selected from the group consisting of hypertension, hypercholesterolemia, hypertriglyceridemia, and obesity as part of the Metabolic Syndrome.

5. The method of claim 1, wherein the individual has at least one condition selected from the group consisting of obesity, insulin resistance, hypertension, dyslipidemia, impaired glucose tolerance, accompanied by increased acute phase proteins including C-Reactive Protein and fibrinogen.

6. The method of claim 1, wherein said individual has diabetes mellitus, or coronary artery disease as part of the Metabolic Syndrome.

7. A method for controlling elevated blood glucose level in an individual with inflammation-related metabolic disturbances, comprising:
    administering to said individual an effective dosage of a composition selected from the group consisting of YG-Product, YGG-Product, or a combination thereof.

8. The method of claim 7, wherein the individual has at least one component of the Metabolic Syndrome.

9. A method for mitigating a symptom in a patient having Metabolic Syndrome, said symptom characteristic of chronic inflammation, said patient presenting said symptom, said method comprising administering to the patient a pharmaceutical preparation containing an effective dosage amount of YG-Product, YGG-Product, or a combination thereof.

10. The method of claim 9, wherein said symptom is at least one selected from the group consisting of elevated blood pressure, atherogenic dyslipidemia, abdominal obesity, insulin resistance with or without glucose intolerance, a proinflammatory state, and a prothrombotic state.

11. A method for mitigating a symptom in a patient having Metabolic Syndrome, said symptom characteristic of an inflammation-related metabolic disturbance, said patient presenting said symptom, said method comprising administering to the patient a pharmaceutical preparation containing an effective dosage amount of YG-Product, YGG-Product, or a combination thereof.

12. The method of claim 11, wherein said component is at least one selected from the group consisting of elevated blood pressure, atherogenic dyslipidemia, abdominal obesity, insulin resistance with or without glucose intolerance, a proinflammatory state, and a prothrombotic state.

13. A method for deferring the progression of a patient having Metabolic Syndrome from the Metabolic Syndrome including Hypertension, to Diabetes Mellitus, Coronary Heart Disease, or Cancer, said method comprising administering to the patient a pharmaceutical preparation containing an effective dosage amount of YG-Product, YGG-Product, or a combination thereof.

* * * * *

SEQUENCE LISTING

```
<160> NUMBER OF SEQ ID NOS: 2

<210> SEQ ID NO 1
<211> LENGTH: 5
<212> TYPE: PRT
<213> ORGANISM: Homo sapiens

<400> SEQUENCE: 1

Tyr Gly Gly Phe Met
1               5

<210> SEQ ID NO 2
<211> LENGTH: 5
<212> TYPE: PRT
<213> ORGANISM: Homo sapiens

<400> SEQUENCE: 2

Tyr Gly Gly Phe Leu
1               5
```